(12) United States Patent  
Nakanishi

(10) Patent No.: US 12,185,444 B2
(45) Date of Patent: Dec. 31, 2024

(54) LIGHT SOURCE DEVICE AND SUBJECT OBSERVATION SYSTEM

(71) Applicant: Sony Olympus Medical Solutions Inc., Tokyo (JP)

(72) Inventor: Tatsuya Nakanishi, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 0 days.

(21) Appl. No.: 17/768,475

(22) PCT Filed: Oct. 27, 2020

(86) PCT No.: PCT/JP2020/040303
§ 371 (c)(1),
(2) Date: Apr. 13, 2022

(87) PCT Pub. No.: WO2021/095517
PCT Pub. Date: May 20, 2021

(65) Prior Publication Data
US 2024/0298395 A1    Sep. 5, 2024

(30) Foreign Application Priority Data
Nov. 13, 2019    (JP) .................................. 2019-205724

(51) Int. Cl.
*H05B 47/16* (2020.01)
*A61B 1/06* (2006.01)
(Continued)

(52) U.S. Cl.
CPC ........... *H05B 47/16* (2020.01); *H05B 47/105* (2020.01); *H05B 47/155* (2020.01); *H05B 47/17* (2020.01); *A61B 1/0655* (2022.02); *A61B 1/0661* (2013.01)

(58) Field of Classification Search
CPC ...... H05B 47/16; H05B 47/17; H05B 47/155; H05B 47/105; A61B 1/0655; A61B 1/0661
See application file for complete search history.

(56) References Cited

U.S. PATENT DOCUMENTS

2012/0123213 A1    5/2012  Seto
2012/0241620 A1    9/2012  On
(Continued)

FOREIGN PATENT DOCUMENTS

JP    2007-500546 A    1/2007
JP    2013-168585 A    8/2013
(Continued)

OTHER PUBLICATIONS

International Search Report and Written Opinion mailed on Jan. 19, 2021, received for PCT Application PCT/JP2020/040303, Filed on Oct. 27, 2020, 8 pages including English Translation.

*Primary Examiner* — Monica C King
(74) *Attorney, Agent, or Firm* — XSENSUS LLP

(57) ABSTRACT

A light source device includes a first light source, a second light source, and a light source control unit. The first light source emits laser light. The second light source emits light. The light source control unit controls the operations of the first and second light sources. The light source control unit executes each of first switching control and second switching control on laser light which is applied to a subject after emitted from the first light source based on a time reference in accordance with a class specified by a laser standard indicating a safety standard for laser products. In the first switching control, a lighting state is switched from the first light source to the second light source. In the second switching control, the lighting state is switched from the second light source to the first light source.

12 Claims, 10 Drawing Sheets

(51) Int. Cl.
*H05B 47/105* (2020.01)
*H05B 47/155* (2020.01)
*H05B 47/17* (2020.01)

(56) References Cited

U.S. PATENT DOCUMENTS

2014/0347430 A1 11/2014 Maeda et al.
2017/0353672 A1 12/2017 Nakamura
2019/0076119 A1 3/2019 Yang et al.

FOREIGN PATENT DOCUMENTS

| JP | 2015523137 A | 8/2015 |
| JP | 2016-194981 A | 11/2016 |
| JP | 6392887 B2 | 9/2018 |
| JP | 2019080624 A | 5/2019 |
| JP | 2019194546 A | 11/2019 |
| WO | 2014/020728 A1 | 2/2014 |
| WO | WO2016067316 A1 | 9/2017 |
| WO | 2017/212582 A1 | 12/2017 |

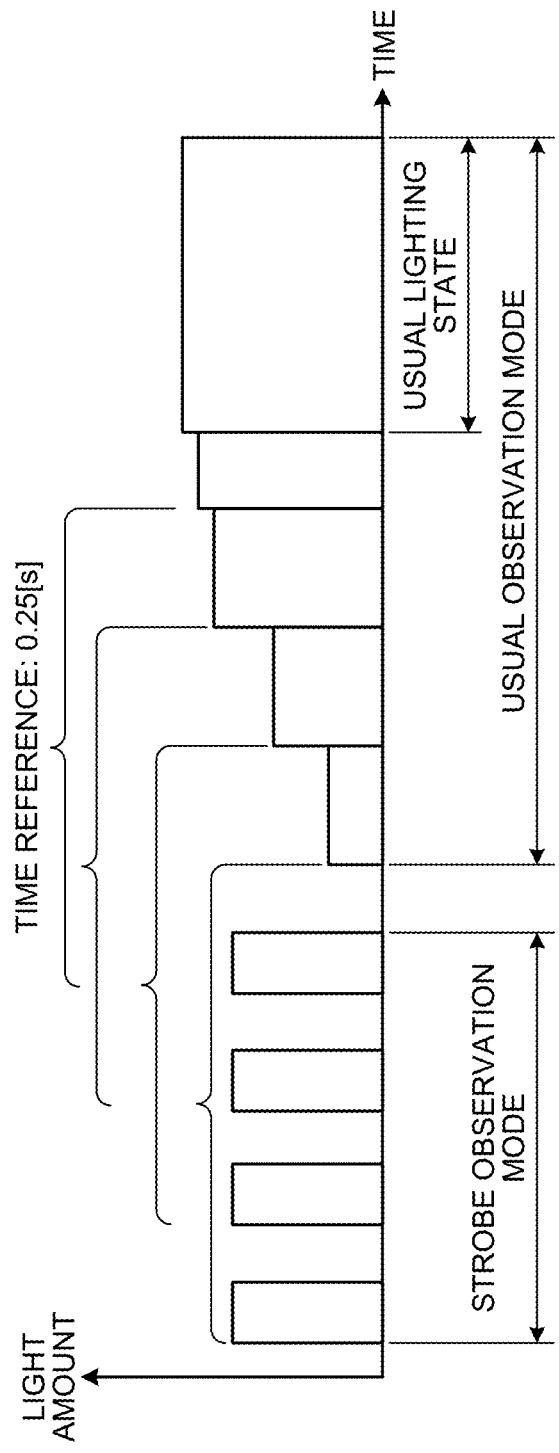

LIGHT SOURCE DEVICE AND SUBJECT OBSERVATION SYSTEM

CROSS-REFERENCE TO RELATED APPLICATIONS

The present application is based on PCT filing PCT/JP2020/040303, filed Oct. 27, 2020, which claims priority to Japanese Application No. 2019-205724, filed Nov. 13, 2019, the entire contents of each are incorporated herein by reference.

FIELD

The present disclosure relates to a light source device and a subject observation system.

BACKGROUND

Laser products for observing a subject by applying laser light to the subject have been known (e.g., see Patent Literature 1).

In the laser product described in Patent Literature 1, the light amount of laser light emitted within a certain period is limited to a reference value or less in order to satisfy requirements specified by a laser standard indicating a safety standard for laser products and secure safety.

CITATION LIST

Patent Literature

Patent Literature 1: Japanese Patent No. 6392887

SUMMARY

Technical Problem

By the way, a laser product for observing a subject by applying laser light to the subject needs as high a light amount as possible. When protective glasses for protecting eyes from laser light are required to be worn, however, the protective glasses make color look different from the actual color, and reduces observation performance. That is, as high a light amount as possible is desired within a range in which safety is secured without wearing the protective glasses.

Here, a laser product capable of switching between laser light and, for example, light emitting diode (LED) light is assumed. If laser light and LED light are mixed within a time reference in accordance with a class specified by a laser standard to the laser light at the time of switching between the laser light and the LED light, an exposure emission amount (AE) is larger than that in a lighting state of the laser light alone, which may cause the laser product to proceed to a class in which protective glasses are required to be worn.

Thus, in the laser product, there is a demand for a technique capable of securing the light amount of emitted light while securing safety.

The present disclosure has been made in view of the above-described situation, and an object of the present disclosure is to provide a light source device and a subject observation system capable of securing the light amount of emitted light while securing safety.

Solution to Problem

To solve the above-described problem and achieve the object, a light source device according to the present disclosure includes: a first light source configured to emit laser light; a second light source configured to emit light; and a light source control unit configured to control operations of the first light source and the second light source, wherein the light source control unit is configured to execute each of first switching control of switching a lighting state from the first light source to the second light source and second switching control of switching the lighting state from the second light source to the first light source on laser light which is applied to a subject after emitted from the first light source based on a time reference in accordance with a class specified by a laser standard indicating a safety standard for a laser product.

Moreover, in the above-described light source device according to the present disclosure, the second light source is turned on after time of the time reference or more has elapsed since the first light source was turned off in the first switching control, and the first light source is turned on after the time of the time reference or more has elapsed since the second light source was turned off in the second switching control.

Moreover, the above-described light source device according to the present disclosure further includes a light amount detecting unit configured to detect a light amount of laser light emitted from the first light source and a light amount of light emitted from the second light source, and in the first switching control, a light amount of the second light source is adjusted based on a total light amount of light detected by the light amount detecting unit from a time point earlier than a present time by the time reference to the present time during a period from when the first light source was turned off to when the time reference has elapsed and an exposure emission limit set in accordance with the class, and in the second switching control, a light amount of the first light source is adjusted based on a total light amount of light detected by the light amount detecting unit from a time point earlier than a present time by the time reference to the present time during a period from when the second light source was turned off to when the time reference has elapsed and the exposure emission limit.

A light source device according to the present disclosure includes: first light source configured to emit laser light; a second light source configured to emit light; and a light source control unit configured to control operations of the first light source and the second light source, wherein the light source control unit is configured to execute switching control of switching a lighting state from the first light source to the second light source on laser light applied to a subject after emitted from the first light source based on a time reference in accordance with a class specified by a laser standard indicating a safety standard for a laser product.

In the above-described light source device according to the present disclosure, the second light source is turned on after time of the time reference or more has elapsed since the first light source was turned off in the switching control.

The above-described light source device according to the present disclosure, further includes a light amount detecting unit configured to detect a light amount of laser light emitted from the first light source and a light amount of light emitted from the second light source, and in the switching control, a light amount of the second light source is adjusted based on a total light amount of light detected by the light amount detecting unit from a time point earlier than a present time by the time reference to the present time during a period from when the first light source was turned off to when the time reference has elapsed and an exposure emission limit set in accordance with the class.

A light source device according to the present disclosure includes: a first light source configured to emit laser light; a second light source configured to emit light; and a light source control unit configured to control operations of the first light source and the second light source, wherein the light source control unit is configured to execute switching control of switching a lighting state from the second light source to the first light source on laser light applied to a subject after emitted from the first light source based on a time reference in accordance with a class specified by a laser standard indicating a safety standard for a laser product.

In the above-described light source device according to the present disclosure, in the switching control, the first light source is turned on after time of the time reference or more has elapsed since the second light source was turned off.

The above-described light source device according to the present disclosure further includes a light amount detecting unit configured to detect a light amount of laser light emitted from the first light source and a light amount of light emitted from the second light source, and in the switching control, a light amount of the first light source is adjusted based on a total light amount of light detected by the light amount detecting unit from a time point earlier than a present time by the time reference to the present time during a period from when the second light source was turned off to when the time reference has elapsed and an exposure emission limit set in accordance with the class.

In the above-described light source device according to the present disclosure, the class is a class 2 or class 2M specified by the laser standard or a class 3R of a wavelength range of 400 to 700 nm.

In the above-described light source device according to the present disclosure, the light source control unit is configured to emit laser light from the first light source in a pulse form.

A subject observation system according to the present disclosure includes: the above-described light source device; and an imaging device configured to capture an image of a subject illuminated with light from the light source device.

Advantageous Effects of Invention

According to a light source device and a subject observation system of the present disclosure, the light amount of emitted light can be secured while securing safety.

BRIEF DESCRIPTION OF DRAWINGS

FIG. 10 illustrates the first switching control.

DESCRIPTION OF EMBODIMENTS

Figure 1:
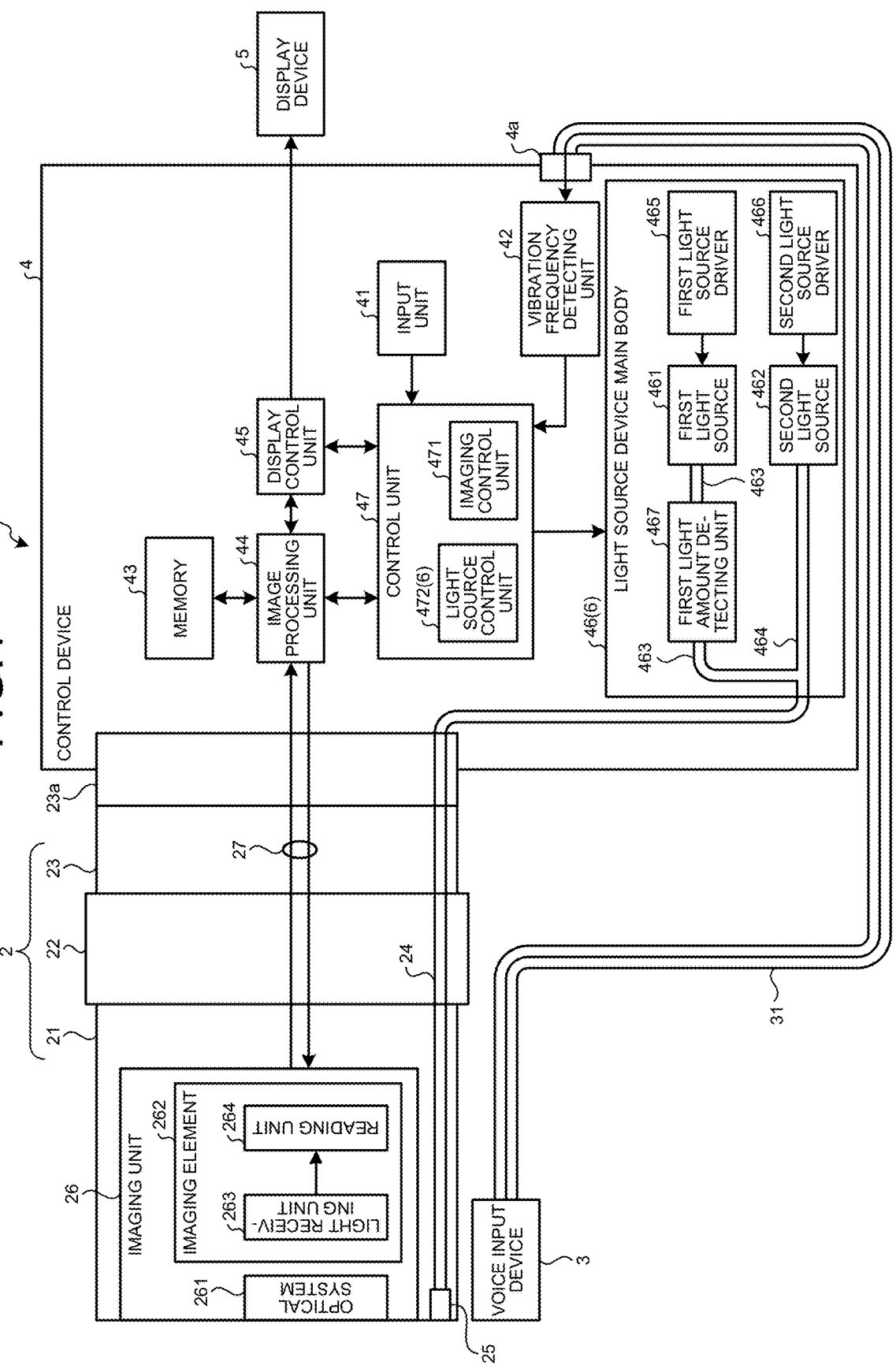
FIG. 1 is a block diagram illustrating a subject observation system according to a first embodiment.

Embodiments for carrying out the present disclosure (hereinafter, embodiments) will be described below with reference to the drawings. Note that the present disclosure is not limited by the embodiments described below. Moreover, in the drawings, the same reference signs are given to the same parts.

First Embodiment

[Schematic Configuration of Subject Observation System]

FIG. 1 is a block diagram illustrating a subject observation system 1 according to the first embodiment.

The subject observation system 1 is a strobe endoscope system used in the medical field to observe the vocal cords that are a subject (object). As illustrated in FIG. 1, the subject observation system 1 includes an endoscope 2, a voice input device 3, a control device 4, and a display device 5.

The endoscope 2 captures an object image from a subject. As illustrated in FIG. 1, the endoscope 2 includes an insertion portion 21, an operating unit 22, and a universal cord 23.

The insertion portion 21 has an elongated shape. As illustrated in FIG. 1, a light guide 24, which is an illumination fiber, is inserted through the insertion portion 21. Furthermore, an illumination lens 25 is provided at the distal end portion of the insertion portion 21 so as to face the exit end of the light guide 24. Then, light emitted from the light guide 24 is emitted from the distal end of the insertion portion 21 via the illumination lens 25.

Furthermore, as illustrated in FIG. 1, an imaging unit 26 is provided at the distal end portion of the insertion portion 21.

The imaging unit 26 captures light (object image), which is applied to a subject via the illumination lens 25 and reflected by the subject, into the insertion portion 21, and captures the object image. As illustrated in FIG. 1, the imaging unit 26 includes an optical system 261 and an imaging element 262.

The optical system 261 includes one or a plurality of lenses. The optical system 261 captures an object image from the subject into the insertion portion 21, and forms an image on a light receiving surface of the imaging element 262 (light receiving unit 263).

Under the control of the control device 4, the imaging element 262 sequentially captures the object image formed by the optical system 261 at a specific frame rate. As illustrated in FIG. 1, the imaging element 262 includes the light receiving unit 263 and a reading unit 264.

A plurality of pixels is arranged on the light receiving surface of the light receiving unit 263. The plurality of pixels receives the object image formed by the optical system 261, and generates a pixel signal by performing photoelectric conversion on the received object image. The plurality of pixels is arranged in a matrix so that a plurality of pixel rows (horizontal lines) is arranged in a vertical direction. The plurality of pixel rows (horizontal lines) includes two or more pixels arranged along a horizontal direction. Then, the light receiving unit 263 generates a pixel signal representing the subject from the object image formed on the light receiving surface.

The reading unit 264 exposes a plurality of pixels in the light receiving unit 263, and reads pixel signals from the plurality of pixels.

The above-described imaging element 262 can include a complementary metal oxide semiconductor (CMOS) imaging element or a charge coupled device (CCD) imaging element. The CMOS imaging element generates a pixel signal by a rolling shutter method. The CCD imaging element generates a pixel signal by a global shutter method.

Furthermore, as illustrated in FIG. 1, an electric cable 27 is inserted into the insertion portion 21. The electric cable 27 transmits a pixel signal and a control signal, for example. That is, the imaging unit 26 generates a pixel signal by the rolling shutter method or the global shutter method in accordance with a control signal transmitted from the control device 4 via the electric cable 27, and outputs the pixel signal to the control device 4 via the electric cable 27.

The operating unit 22 is connected to the side of the proximal end of the insertion portion 21, and provided with various switches (not illustrated) that receive a user operation of a user such as a doctor. In the first embodiment, the operating unit 22 is provided with switches that receive a first user operation and a second user operation. The subject observation system 1 is set to a strobe observation mode by the first user operation. The subject observation system 1 is set to a usual observation mode by the second user operation. Here, in the strobe observation mode, pulse light, which is laser light, is applied to the vocal cords to observe the vocal cords. In contrast, in the usual observation mode, white light, which is LED light, is applied to a subject to observe the subject. Then, the operating unit 22 outputs an operation signal in response to the user operation to the control device 4 via the electric cable 27.

The universal cord 23 extends from the operating unit 22, and is provided with the light guide 24, the electric cable 27, and the like. Then, the proximal end of the universal cord 23 is connected to the control device 4 by a connector 23a.

As illustrated in FIG. 1, the voice input device 3 is connected to a voice input terminal 4a of the control device 4 via a cord 31. The voice input device 3 inputs voice, and outputs a voice signal. Then, the voice signal is output to the control device 4 via the cord 31.

Note that the voice input device 3 may be configured to operate only when the subject observation system 1 is in the strobe observation mode under the control of the control device 4. Alternatively, the voice input device 3 may be configured to operate even when the subject observation system 1 is in any of the strobe observation mode and the usual observation mode.

The control device 4 includes a central processing unit (CPU), a field-programmable gate array (FPGA), and the like, and comprehensively controls the operations of the imaging unit 26 and the display device 5. Note that the detailed configuration of the control device 4 will be described in "Configuration of Control Device" described later.

The display device 5 includes a display formed of liquid crystal, organic electro luminescence (EL), or the like. The display device 5 displays an image based on a display image signal from the control device 4 under the control of the control device 4.

[Configuration of Control Device]

Next, the configuration of the control device 4 will be described.

As illustrated in FIG. 1, the control device 4 includes an input unit 41, a vibration frequency detecting unit 42, a memory 43, an image processing unit 44, a display control unit 45, a light source device main body 46, and a control unit 47.

The input unit 41 includes an operation device such as a mouse, a keyboard, and a touch panel, and receives a user operation from a user such as a doctor. Then, the input unit 41 outputs an operation signal in response to the user operation to the control unit 47.

The vibration frequency detecting unit 42 detects the frequency of voice (vibration frequency of vocal cords) input to the voice input device 3 based on a voice signal output from the voice input device 3. Then, the vibration frequency detecting unit 42 outputs the detected voice frequency to the control unit 47.

Note that the vibration frequency detecting unit 42 may be configured to operate only when the subject observation system 1 is in the strobe observation mode under the control of the control unit 47. Alternatively, the vibration frequency detecting unit 42 may be configured to operate even when the subject observation system 1 is in any of the strobe observation mode and the usual observation mode.

The memory 43 includes, for example, a dynamic random access memory (DRAM). The memory 43 temporarily stores a plurality of frames of pixel signals sequentially read from the reading unit 264. Furthermore, the memory 43 temporarily stores a plurality of frames of pseudo pixel signals, which will be described later, generated by the image processing unit 44.

When the subject observation system 1 is in the strobe observation mode, the image processing unit 44 performs the following processing under the control of the control unit 47.

That is, the image processing unit 44 generates a pseudo pixel signal from a plurality of consecutive frames of pixel signals stored in the memory 43. The pseudo pixel signal corresponds to a pixel signal in the case where all pixels of the light receiving unit 263 are exposed during a period of illumination of pulse light (laser light) performed by the light source device main body 46. Note that a known generation method (e.g., see Japanese Patent No. 5948512) can be adopted as a method of generating the pseudo pixel signal (pixel signal at illumination).

Furthermore, the image processing unit 44 performs the following processing under the control of the control unit 47 even when the subject observation system 1 is in any of the strobe observation mode and the usual observation mode.

That is, the image processing unit 44 performs predetermined image processing on pixel signals of a plurality of pixels read by the reading unit 264. For example, the image processing unit 44 performs image processing on a pixel signal. The image processing includes optical black subtraction processing, white balance (WB) adjustment processing, demosaic processing (in case where imaging element 262 includes a Bayer array color filter (not illustrated)), color matrix calculation processing, gamma correction processing, color reproduction processing, edge enhancement processing, and the like.

When the subject observation system 1 is in the strobe observation mode, the display control unit 45 generates a display image signal as illustrated below under the control of the control unit 47.

That is, the display control unit 45 generates a display image signal to be displayed on the display device 5 from each pseudo pixel signal by pulse light (laser light) included in a display cycle of the display device 5. Note that a known generation method (e.g., see Japanese Patent No. 5948512) can be adopted as a method of generating the display image signal.

Furthermore, when the subject observation system 1 is in the usual observation mode, the display control unit 45 generates the display image signal to be displayed on the display device 5 from a pixel signal, on which the image processing is performed by the image processing unit 44, under the control of the control unit 47.

As illustrated in FIG. 1, the light source device main body 46 includes first and second light sources 461 and 462, first and second light guide paths 463 and 464, first and second light source drivers 465 and 466, and a first light amount detecting unit 467. Note that, although the light source device main body 46 is built in the control device 4 in the first embodiment, this is not a limitation. The light source device main body 46 may be independent of the control device 4.

The first light source 461 includes a semiconductor laser, and emits pulse light (laser light) in response to supplied drive current (pulse current).

In the first embodiment, a semiconductor laser is used in the first light source 461. In the semiconductor laser, the subject observation system 1 is a laser product of a class 2, a class 2M, or a class 3R. The class 2 and the class 2M are specified by a laser standard (e.g., IEC60825-1: 2014) indicating "safety standard for laser products". The class 3R has a wavelength range of 400 to 700 nm. Here, a class of the laser product is determined based on laser light emitted from the first light source 461 and then emitted from the distal end of the insertion portion 21. Note that protective glasses are not required to be worn for the laser products of the class 2, the class 2M, and the class 3R of the wavelength range of 400 to 700 nm.

The second light source 462 includes an LED that emits white light, and emits white light (LED light) in response to the supplied drive current.

The first light guide path 463 includes, for example, an optical fiber and the like, and guides pulse light (laser light) emitted from the first light source 461 to the incident end of the light guide 24. Then, the pulse light (laser light) is emitted from the distal end of the insertion portion 21 via the light guide 24 and the illumination lens 25.

The second light guide path 464 includes, for example, an optical fiber and the like, and guides white light (LED light) emitted from the second light source 462 to the incident end of the light guide 24. Then, the white light (LED light) is emitted from the distal end of the insertion portion 21 via the light guide 24 and the illumination lens 25.

The first light source driver 465 supplies drive current (pulse current) to the first light source 461 under the control of the control unit 47. Note that the first light source driver 465 operates only when the subject observation system 1 is in the strobe observation mode under the control of the control unit 47. That is, the first light source 461 emits pulse light (laser light) only when the subject observation system 1 is in the strobe observation mode.

The second light source driver 466 supplies drive current to the second light source 462 under the control of the control unit 47. Note that the second light source driver 466 operates only when the subject observation system 1 is in the usual observation mode under the control of the control unit 47. That is, the second light source 462 emits white light (LED light) only when the subject observation system 1 is in the usual observation mode.

The first light amount detecting unit 467 corresponds to the light amount detecting unit according to the present disclosure. The first light amount detecting unit 467 includes, for example, a photodiode and the like, and is installed in the first light guide path 463. Then, the first light amount detecting unit 467 receives a part of the pulse light (laser light), which is emitted from the first light source 461 and follows the first light guide path 463, and detects the light amount of the pulse light (laser light) under the control of the control unit 47.

The control unit 47 includes, for example, a CPU, an FPGA, and the like. The control unit 47 controls the operations of the imaging unit 26 and the display device 5 while controlling the operation of the entire control device 4. Furthermore, the control unit 47 sets the subject observation system 1 to one of the strobe observation mode and the usual observation mode in response to the first and second user operations on the operating unit 22 performed by a user such as a doctor. As illustrated in FIG. 1, the control unit 47 includes an imaging control unit 471 and a light source control unit 472.

The imaging control unit 471 performs exposure control by the rolling shutter method or the global shutter method on the imaging element 262 at a specific frame rate. When the subject observation system 1 is in the usual observation mode, the light source control unit 472 controls the operation of the second light source driver 466, and causes the second light source 462 to emit white light (LED light). In contrast, when the subject observation system 1 is in the strobe observation mode, the light source control unit 472 controls the operation of the first light source driver 465, and causes the first light source 461 to emit pulse light (laser light) so as to synchronize with the frequency of voice emitted from the vocal cords detected by the vibration frequency detecting unit 42.

The light source device main body 46 and the light source control unit 472 described above correspond to a light source device 6 (FIG. 1) according to the present disclosure.

[Operation of Control Device]

Next, the operation of the above-described control device 4 will be described with reference to FIG. 2. Note that, for convenience of explanation, a light source control method of controlling the operations of the first and second light sources 461 and 462 will be mainly described below.

Figure 2:
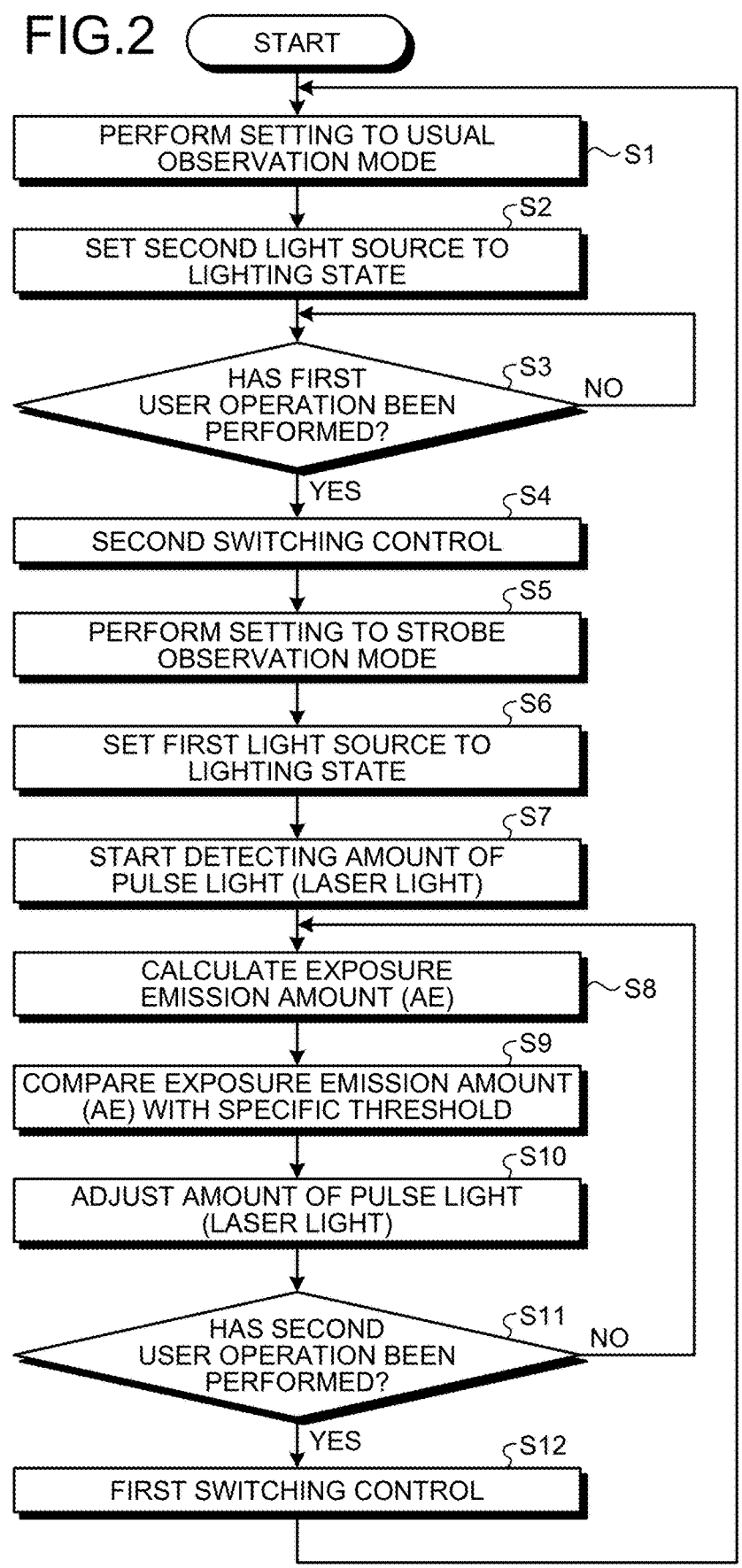
FIG. 2 is a flowchart illustrating a light source control method executed by a control device.

FIG. 2 is a flowchart illustrating a light source control method executed by the control device 4.

First, the control unit 47 sets the subject observation system 1 to the usual observation mode after the subject observation system 1 is activated (Step S1). Then, at the same time that the subject observation system 1 is set to the usual observation mode, the light source control unit 472 controls the operation of the second light source driver 466, and causes the second light source 462 to emit white light (LED light) (Step S2).

In the usual observation mode, a user such as a doctor brings the distal end of the insertion portion 21 closer to the vocal cords while checking the captured image obtained by capturing an object image from a subject, on which white light is applied, on a screen of the display device 5. Then, the user such as a doctor performs the first user operation on the operating unit 22 after bringing the distal end of the insertion portion 21 closer to the vocal cords.

After Step S2, the control unit 47 constantly monitors whether or not the first user operation has been performed (Step S3).

When it is determined that the first user operation has been performed (Step S3: Yes), the control unit 47 sets the subject observation system 1 to the strobe observation mode (Step S5). Then, at the same time that the subject observation system 1 is set to the strobe observation mode, the light source control unit 472 controls the operation of the first light source driver 465, and causes the first light source 461 to emit pulse light (laser light) so as to synchronize with the frequency of voice emitted from the vocal cords detected by the vibration frequency detecting unit 42 (Step S6).

Here, when the control unit 47 switches the subject observation system 1 from the usual observation mode to the strobe observation mode, the light source control unit 472 executes second switching control of switching a lighting state from the second light source 462 to the first light source 461 (Step S4).

Figure 3:
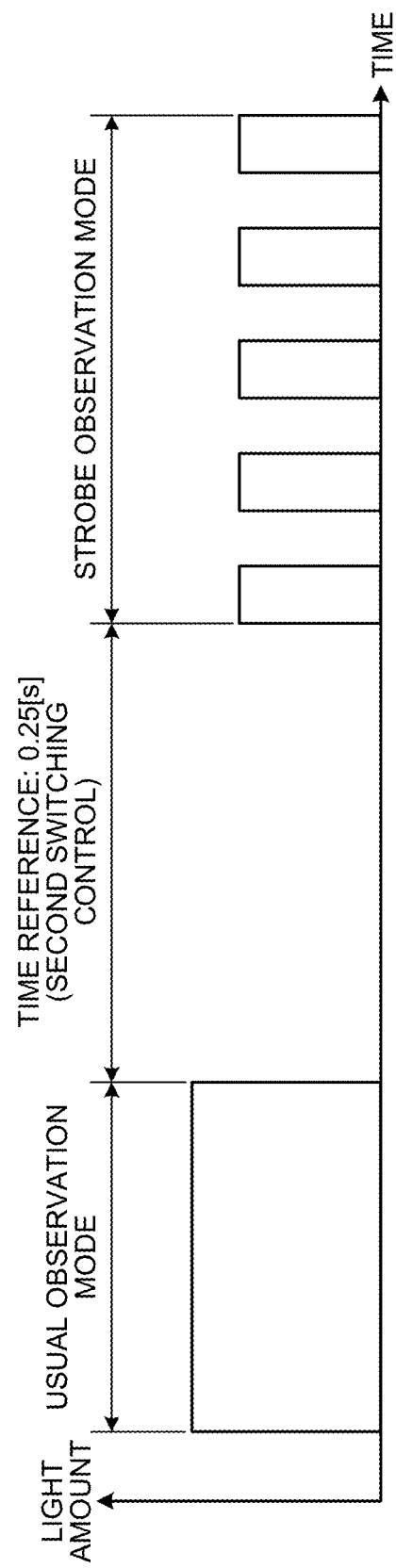
FIG. 3 illustrates second switching control.

FIG. 3 illustrates the second switching control. Specifically, in FIG. 3, the vertical axis represents the light amount of light emitted from the first and second light sources 461 and 462, and the horizontal axis represents time.

In the second switching control according to the first embodiment, as illustrated in FIG. 3, the first light source 461 is turned on after a time reference has elapsed since the second light source 462 was turned off. The time reference is specified by a laser standard (e.g., IEC60825-1: 2014) indicating "safety standard for laser products" to the class 2 or the class 2M of the subject observation system 1 (laser product) or the class 3R of a wavelength range of 400 to 700 nm. The time reference is 0.25 [s].

Furthermore, the light source control unit 472 controls the operation of the first light amount detecting unit 467 at the same time as the emission of the pulse light (laser light) from the first light source 461 (Step S6), and starts detection of the light amount of the pulse light (laser light) (Step S7).

After Step S7, the light source control unit 472 converts the total light amount of light detected by the first light amount detecting unit 467 from the time point earlier than the present time by the above-described time reference (0.25 [s]) to the present time into a light amount of light emitted from the distal end of the insertion portion 21 (hereinafter, referred to as distal end emitted light amount). Furthermore, the light source control unit 472 calculates an exposure emission amount (AE) specified by the laser standard (e.g., IEC60825-1: 2014) indicating "safety standard for laser products" by using the distal end emitted light amount, beam divergence (design value), and the like in consideration of a measurement condition (e.g., measurement distance) described in the laser standard (Step S8).

After Step S8, the light source control unit 472 compares the exposure emission amount (AE) calculated in Step S8 with a specific threshold (Step S9). The light source control unit 472 adjusts the light amount of pulse light (laser light) emitted from the first light source 461 at the present time so that the exposure emission amount does not exceed the specific threshold (Step S10).

Here, the specific threshold is the lowest value obtained by calculating "$AEL_{single}$", "$AEL_{s.p.train}$", and "$AEL_{s.p.T}$", which is an exposure emission limit (AEL) specified by the laser standard (e.g., IEC60825-1: 2014) indicating "safety standard for laser products".

Note that the "$AEL_{single}$", "$AEL_{s.p.train}$", and "$AEL_{s.p.T}$" can be calculated by using the wavelength of pulse light (laser light), emission duration, a light source size, the frequency of pulse light (laser light), the time reference, and the like.

After Step S10, the control unit 47 constantly monitors whether or not the second user operation has been performed (Step S11).

If it is determined that the second user operation has not been performed (Step S11: No), the control unit 47 returns to Step S8.

In contrast, if it is determined that the second user operation has been performed (Step S11: Yes), the control unit 47 returns to Step S1. That is, Steps S8 to S10 are repeatedly executed at specific time intervals.

Here, when the control unit 47 switches the subject observation system 1 from the strobe observation mode to the usual observation mode, the light source control unit 472 executes first switching control of switching a lighting state from the first light source 461 to the second light source 462 (Step S12).

Figure 4:
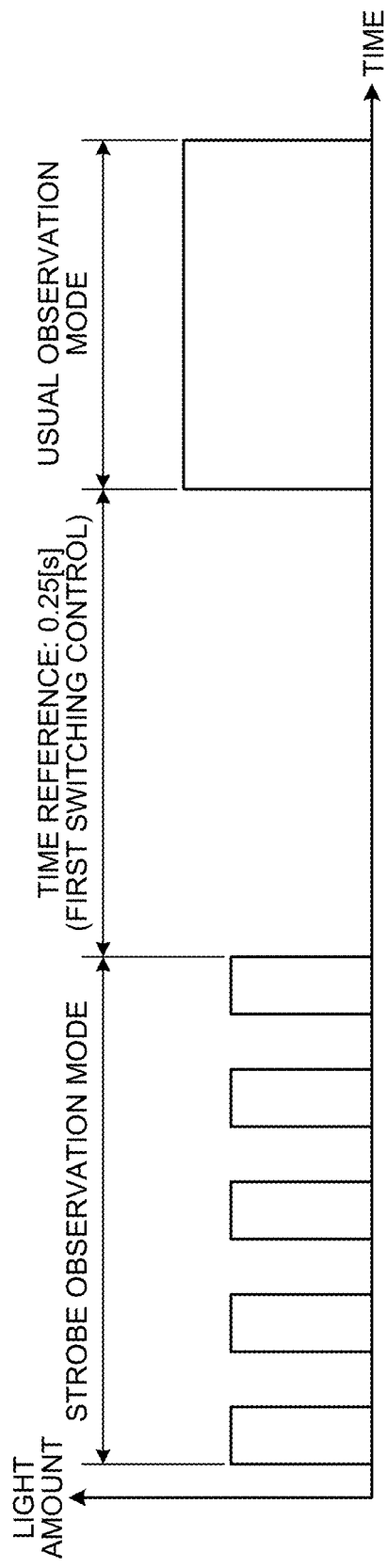
FIG. 4 illustrates first switching control.

FIG. 4 illustrates the first switching control. Specifically, in FIG. 4, the vertical axis represents the light amount of light emitted from the first and second light sources 461 and 462, and the horizontal axis represents time.

In the first switching control according to the first embodiment, as illustrated in FIG. 4, the second light source 462 is turned on after a time reference has elapsed since the first light source 461 was turned off. The time reference is the same as the time reference used in the second switching control, and is 0.25 [s].

According to the above-described first embodiment, the following effects are exhibited.

The subject observation system 1 (light source device 6) according to the first embodiment executes the first switching control in which the second light source 462 is turned on after a time reference (0.25 [s]) has elapsed since the first light source 461 was turned off. Furthermore, the subject observation system 1 (light source device 6) executes the second switching control in which the first light source 461 is turned on after a time reference (0.25 [s]) has elapsed since the second light source 462 was turned off. That is, at the time of switching between pulse light (laser light) and white light (LED light), the pulse light (laser light) and the white light (LED light) are not mixed in the time reference (0.25 [s]). Thus, the subject observation system 1 does not shift from the class 2, the class 2M, or the class 3R of the wavelength range of 400 to 700 nm, in which wearing protective glasses is unnecessary, to a class (e.g., class 3B and class 4) in which wearing protective glasses is necessary.

Therefore, the subject observation system 1 (light source device 6) according to the first embodiment can secure the light amount of emitted light while securing safety.

Second Embodiment

Next, a second embodiment will be described.

In the following description, the same reference signs are attached to configurations similar to those in the above-described first embodiment, and detailed description thereof will be omitted or simplified.

Figure 5:
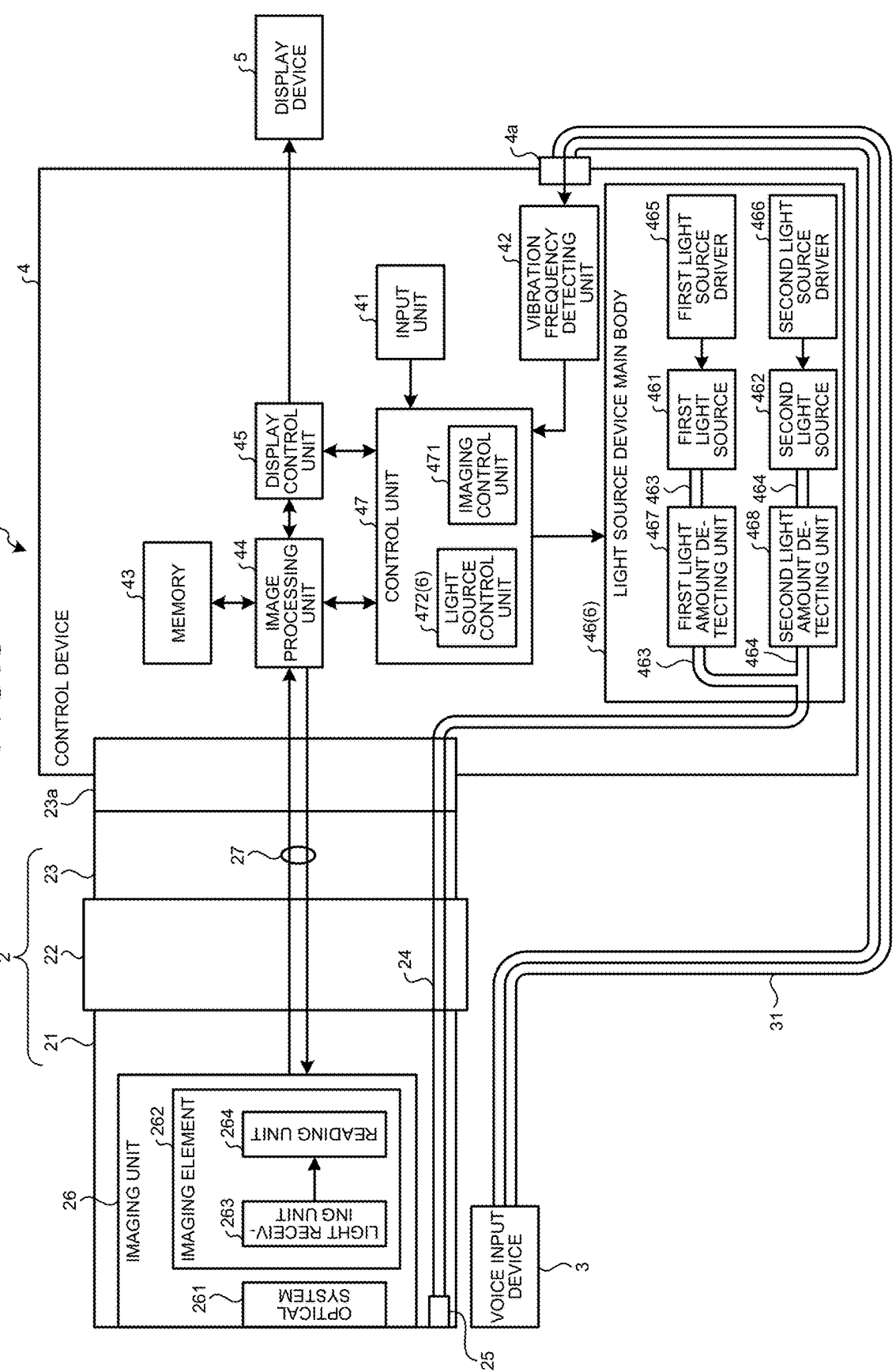
FIG. 5 is a block diagram illustrating a subject observation system according to a second embodiment.
Figure 6:
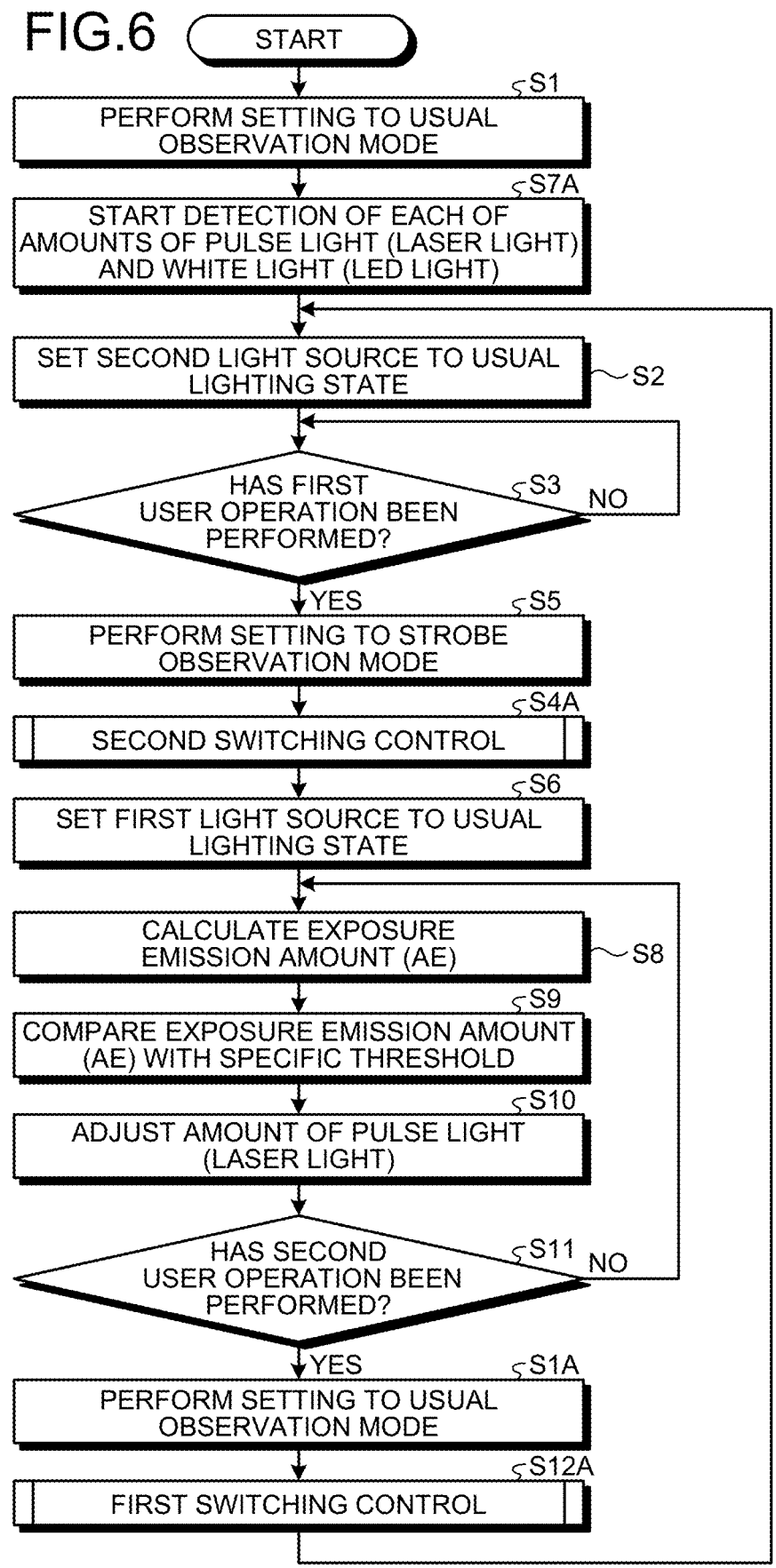
FIG. 6 is a flowchart illustrating a light source control method executed by a control device.

FIG. 5 is a block diagram illustrating a subject observation system 1A according to the second embodiment. FIG. 6 is a flowchart illustrating a light source control method executed by the control device 4.

As illustrated in FIG. 5, the subject observation system 1A according to the second embodiment is obtained by adding a second light amount detecting unit 468 to the light source device main body 46 of the subject observation system 1 described in the above-described first embodiment.

The second light amount detecting unit 468 corresponds to the light amount detecting unit according to the present disclosure. The second light amount detecting unit 468 includes, for example, a photodiode and the like, and is installed in the second light guide path 464. Then, the second light amount detecting unit 468 receives a part of white light (LED light), which is emitted from the second light source 462 and follows the second light guide path 464, and detects the light amount of the white light (LED light) under the control of the control unit 47.

Then, as illustrated in FIG. 6, the control device 4 according to the second embodiment executes a light source control method different from the light source control method described in the above-described first embodiment.

In the light source control method according to the second embodiment (FIG. 2), as illustrated in FIG. 6, Steps S4A, S7A, and S12A are adopted instead of Steps S4, S7, and S12, and Step S1A is added to the light source control method described in the above-described first embodiment. Thus, only Steps S1A, S4A, S7A, and S12A will be mainly described below.

Step S7A is executed at the same time as Step S1.

Specifically, in Step S7A, the light source control unit 472 controls each of the operations of the first and second light amount detecting units 467 and 468, and starts detection of each of the light amounts of pulse light (laser light) and white light (LED light). Then, the control unit 47 proceeds to Step S2.

In the second embodiment, when it is determined that the first user operation has been performed (Step S3: Yes), the control unit 47 proceeds to Step S5. Then, at the same time as Step S5, the light source control unit 472 executes the second switching control of switching the lighting state from the second light source 462 to the first light source 461 (Step S4A).

Figure 7:
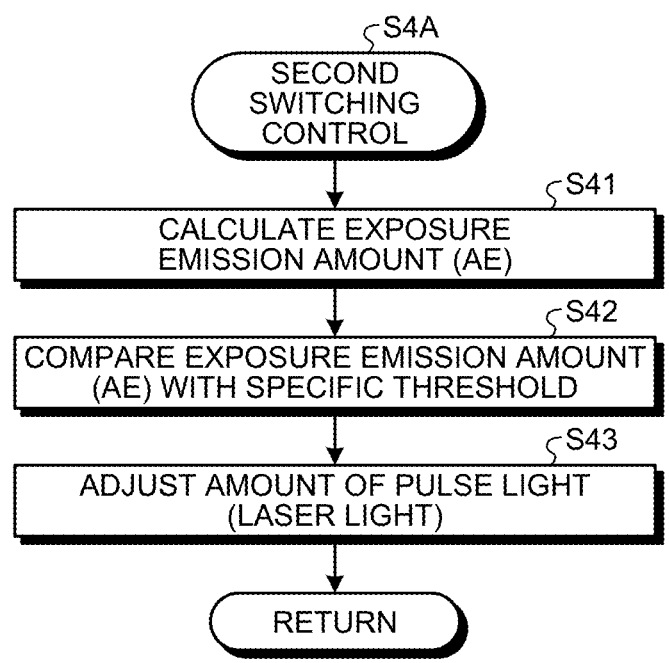
FIG. 7 is a flowchart illustrating the second switching control.
Figure 8:
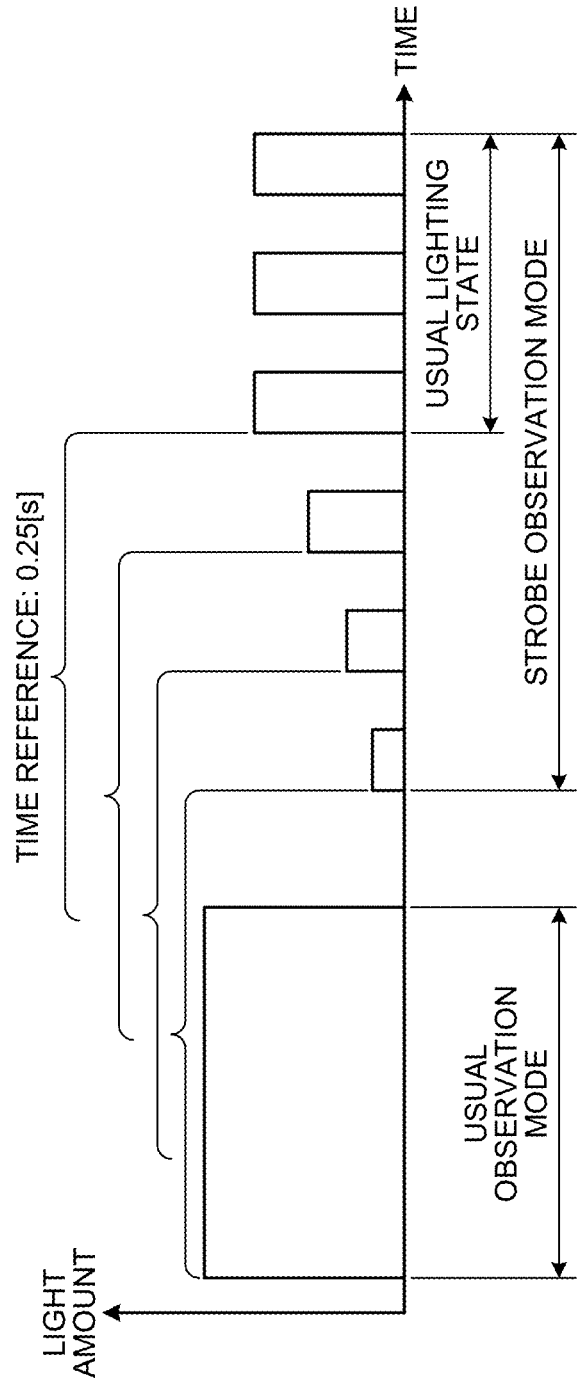
FIG. 8 illustrates the second switching control.

FIG. 7 is a flowchart illustrating the second switching control. FIG. 8 illustrates the second switching control. Specifically, in FIG. 8, the horizontal axis represents the light amount of light emitted from the first and second light sources 461 and 462, and the horizontal axis represents time.

First, as in Step S8, the light source control unit 472 converts the total light amount of light detected by the first and second light amount detecting units 467 and 468 from the time point earlier than the present time by the time reference (0.25 [s]) to the present time into a distal end emitted light amount. Furthermore, the light source control unit 472 calculates the exposure emission amount (AE) by using the distal end emitted light amount, the beam divergence (design value), and the like (Step S41).

After Step S41, the light source control unit 472 compares the exposure emission amount (AE) calculated in Step S41 as in Step S9 with a specific threshold (Step S42). The light source control unit 472 adjusts the light amount of pulse light (laser light) emitted from the first light source 461 at the present time so that the exposure emission amount does not exceed the specific threshold as in Step S10 (Step S43).

Steps S41 to S43 described above are repeatedly executed at specific time intervals during the period from when the second light source 462 was turned off to when the time reference (0.25 [s]) has elapsed. Thus, as illustrated in FIG. 8, the light amount of pulse light (laser light) emitted from the first light source 461 gradually increases in the above-described period.

Then, the control unit 47 proceeds to Step S6 after Step S4A. Note that, in FIGS. 7 and 8, the lighting state of the first light source 461 in Step S6 is described as "usual" in order to distinguish the state from the lighting state of the first light source 461 in Step S4A.

Furthermore, the control unit 47 proceeds to Step S8 after Step S6.

Step S1A is executed when it is determined that the second user operation has been performed (Step S11: Yes).

Specifically, in Step S1A, the control unit 47 sets the subject observation system 1A to the usual observation mode as in Step S1. Then, at the same time as Step S1A, the light source control unit 472 executes the first switching control of switching the lighting state from the first light source 461 to the second light source 462 (Step S12A).

Figure 9:
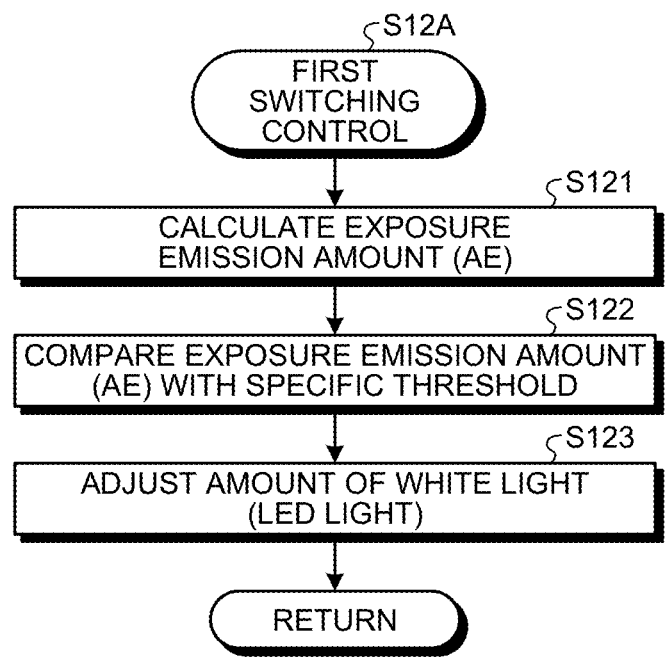
FIG. 9 is a flowchart illustrating the first switching control.

FIG. 9 is a flowchart illustrating the first switching control. FIG. 10 illustrates the first switching control. Specifically, in FIG. 10, the horizontal axis represents the light amount of light emitted from the first and second light sources 461 and 462, and the horizontal axis represents time.

First, as in Step S41, the light source control unit 472 converts the total light amount of light detected by the first and second light amount detecting units 467 and 468 from the time point earlier than the present time by the time reference (0.25 [s]) to the present time into a distal end emitted light amount. Furthermore, the light source control unit 472 calculates the exposure emission amount (AE) by using the distal end emitted light amount, the beam divergence (design value), and the like (Step S121).

After Step S121, the light source control unit 472 compares the exposure emission amount (AE) calculated in Step S121 as in Step S42 with a specific threshold (Step S122). The light source control unit 472 adjusts the light amount of white light (LED light) emitted from the second light source 462 at the present time so that the exposure emission amount does not exceed the specific threshold as in Step S43 (Step S123).

Steps S121 to S123 described above are repeatedly executed at specific time intervals during the period from when the first light source 461 was turned off to when the time reference (0.25 [s]) has elapsed. Thus, as illustrated in FIG. 10, the light amount of white light (LED light) emitted from the second light source 462 gradually increases in the above-described period.

Then, the control unit 47 returns to Step S2 after Step S12A. Note that, in FIGS. 7 and 10, the lighting state of the second light source 462 in Step S2 is described as "usual" in order to distinguish the state from the lighting state of the second light source 462 in Step S12A.

According to the above-described second embodiment, the following effects are exhibited.

The subject observation system 1A (light source device 6) according to the first embodiment executes the first switching control. In the first switching control, the light amount of the second light source 462 is adjusted based on the total light amount of light detected by the first and second light amount detecting units 467 and 468 from the time point earlier than the present time by a time reference (0.25 [s]) to the present time during the period from when the first light source 461 was turned off to when the time reference has elapsed and an exposure emission limit (AEL) set in accordance with the class of the subject observation system 1A. Furthermore, the subject observation system 1A (light source device 6) executes the second switching control. In the second switching control, the light amount of the first light source 461 is adjusted based on the total light amount of light detected by the first and second light amount detecting units 467 and 468 from the time point earlier than the present time by a time reference (0.25 [s]) to the present time during the period from when the second light source 462 was turned off to when the time reference has elapsed and an exposure emission limit (AEL) set in accordance with the class of the subject observation system 1A. That is, even when pulse light (laser light) and white light (LED light) are mixed in the time reference (0.25 [s]) at the time of switching between the pulse light (laser light) and the white light (LED light), the exposure emission amount (AE) does not exceed a specific exposure emission limit (AEL). Thus, the subject observation system 1A does not shift from the class 2, the class 2M, or the class 3R of the wavelength range of 400 to 700 nm, in which wearing protective glasses is unnecessary, to a class (e.g., class 3B and class 4) in which wearing protective glasses is necessary.

Therefore, the subject observation system 1A (light source device 6) according to the second embodiment can secure the light amount of emitted light while securing safety.

In particular, in the second embodiment, pulse light (laser light) and white light (LED light) are mixed during a time reference (0.25 [s]) without providing a turn-off period of the time reference at the time of switching between the pulse light (laser light) and the white light (LED light) unlike the above-described first embodiment. Thus, emitted light can be applied to a subject at an early stage at the time of the switching, and a user such as a doctor can check a captured image in accordance with the emitted light on a screen of the display device 5, which improves convenience.

OTHER EMBODIMENTS

Although the embodiments for carrying out the present disclosure have been described so far, the present disclosure should not be limited only by the above-described first and second embodiments.

Although, in the above-described first and second embodiments, the light source device 6 according to the present disclosure is mounted in the subject observation systems 1 and 1A in which the endoscope 2 is composed of a flexible endoscope, this is not a limitation. For example, the light source device 6 according to the present disclosure may be mounted in a subject observation system in which the endoscope 2 is composed of a rigid endoscope. Furthermore, the light source device 6 according to the present disclosure may be mounted in a subject observation system such as a surgical microscope for magnifying and observing a predetermined visual field area in an object (living body) or on the object (living body surface) (e.g., see JP 2016-42981 A).

Although the light source device 6 according to the above-described first embodiment is provided with the first light amount detecting unit 467, the light source device 6 may have a configuration without the first light amount detecting unit 467.

Although the light source device 6 according to the above-described second embodiment is provided with two of the first and second light amount detecting units 467 and 468, this is not a limitation. The light source device 6 may adopt a configuration in which only one light amount detecting unit is installed in an optical path after the first and second light guide paths 463 and 464 join together. That is, a configuration in which one light amount detecting unit detects the light amounts of pulse light (laser light) and white light (LED light) may be adopted.

Although, in the above-described first and second embodiments, the second light source 462 includes an LED, this is not a limitation. The second light source 462 may include a semiconductor laser as in the first light source 461. Furthermore, although light is continuously emitted from the second light source 462, this is not a limitation. Pulse light may be emitted as in the first light source 461.

Although, in the above-described first and second embodiments, the subject observation systems 1 and 1A observe the vocal cords by strobe, this is not a limitation. The subject observation systems 1 and 1A may observe a subject by special light. Examples of the observation by special light include NBI, IRI, AFI, PDD, and the like.

The NBI is a method of observing the state of blood vessels in a mucosa surface layer and a deeper layer. In the method, narrow-band illumination light having center wavelengths of 415 nm and 540 nm is applied, and the difference in absorption of light of each wavelength to hemoglobin is used.

The IRI is a method of diagnosing the presence or absence of blood flow. In the method, a medical agent called indocyanine green (ICG) with an absorption peak in near-infrared light near a wavelength of 805 nm in the blood is intravenously injected as a contrast medium, excitation light with a center wavelength near 805 nm is applied, and fluorescence from ICG is observed.

The AFI is a method of diagnosing a tumor portion. In the method, a fluorescent agent is preliminarily administered into a subject, a fluorescent image emitted from the subject is observed by applying excitation light, and the presence or absence of the fluorescent image or the shape thereof is observed.

The PDD is a method of acquiring an image, in which cancer cells and normal cells are easily distinguished, by using certain nature. In the nature, although a solution of aminolevulinic acid (5-ALA) taken by a patient is metabolized to the blood raw material (heme) in normal tissues in the body, the solution is not metabolized in cancer cells, and accumulated as an intermediate substance called PpIX. When blue light (center wavelength of 410 nm) is applied to the PpIX, the PpIX emits fluorescent light in red (peak wavelength of 630 nm).

In the light source device 6 according to the above-described first and second embodiments, the lighting state can be switched from the first light source 461 to the second light source 462 while the lighting state can be switched from the second light source 462 to the first light source 461, but this is not a limitation. For example, a light source device capable of switching the lighting state only from the first light source 461 to the second light source 462 may be adopted. In this case, only the first switching control of the first and second switching controls is required to be executable. Furthermore, for example, a light source device capable of switching the lighting state only from the second light source 462 to the first light source 461 may be adopted. In this case, only the second switching control of the first and second switching controls is required to be executable.

In the first switching control according to the above-described first embodiment, the second light source 462 may be turned on after time longer than the time reference (0.25 [s]) has elapsed since the first light source 461 was turned off. Similarly, in the second switching control according to the above-described second embodiment, the first light source 461 may be turned on after time longer than the time reference (0.25 [s]) has elapsed since the second light source 462 was turned off.

Note that the following configurations also belong to the technical scope of the present disclosure.

(1) A light source device according to the present disclosure including: a first light source configured to emit laser light; a second light source configured to emit light; and a light source control unit configured to control operations of the first light source and the second light source, wherein the light source control unit is configured to execute each of first switching control of switching a lighting state from the first light source to the second light source and second switching control of switching the lighting state from the second light source to the first light source on laser light which is applied to a subject after emitted from the first light source based on a time reference in accordance with a class specified by a laser standard indicating a safety standard for a laser product.

(2) The light source device according to (1), wherein the second light source is turned on after time of the time reference or more has elapsed since the first light source was turned off in the first switching control, and the first light source is turned on after the time of the time reference or more has elapsed since the second light source was turned off in the second switching control.

(3) The light source device according to (1), further including a light amount detecting unit configured to detect a light amount of laser light emitted from the first light source and a light amount of light emitted from the second light source, wherein, in the first switching control, a light amount of the second light source is adjusted based on a total light amount of light detected by the light amount detecting unit from a time point earlier than a present time by the time reference to the present time during a period from when the first light source was turned off to when the time reference has elapsed and an exposure emission limit set in accordance with the class, and in the second switching control, a light amount of the first light source is adjusted based on a total light amount of light detected by the light amount detecting unit from a time point earlier than a present time by the time reference to the present time during a period from when the second light source was turned off to when the time reference has elapsed and the exposure emission limit.

(4) A light source device including: a first light source configured to emit laser light; a second light source configured to emit light; and a light source control unit configured to control operations of the first light source and the second light source, wherein the light source control unit is configured to execute switching control of switching a lighting state from the first light source to the second light source on laser light applied to a subject after emitted from the first light source based on a time reference in accordance with a class specified by a laser standard indicating a safety standard for a laser product.

(5) The light source device according to (4), wherein the second light source is turned on after time of the time reference or more has elapsed since the first light source was turned off in the switching control.

(6) The light source device according to (4), further including a light amount detecting unit configured to detect a light amount of laser light emitted from the first light source and a light amount of light emitted from the second light source, wherein, in the switching control, a light amount of the second light source is adjusted based on a total light amount of light detected by the light amount detecting unit from a time point earlier than a present time by the time reference to the present time during a period from when the first light source was turned off to when the time reference has elapsed and an exposure emission limit set in accordance with the class.

(7) A light source device including: a first light source configured to emit laser light; a second light source configured to emit light; and a light source control unit configured to control operations of the first light source and the second light source, wherein the light source control unit is configured to execute switching control of switching a lighting state from the second light source to the first light source on laser light applied to a subject after emitted from the first light source based on a time reference in accordance with a class specified by a laser standard indicating a safety standard for a laser product.

(8) The light source device according to (7), wherein, in the switching control, the first light source is turned on after time of the time reference or more has elapsed since the second light source was turned off.

(9) The light source device according to (7), further including a light amount detecting unit configured to detect a light amount of laser light emitted from the first light source and a light amount of light emitted from the second light source, wherein, in the switching control, a light amount of the first light source is adjusted based on a total light amount of light detected by the light amount detecting unit from a time point earlier than a present time by the time reference to the present time during a period from when the second light source was turned off to when the time reference has elapsed and an exposure emission limit set in accordance with the class.

(10) The light source device according to any one of (1) to (9), wherein the class is a class 2 or class 2M specified by the laser standard or a class 3R of a wavelength range of 400 to 700 nm.

(11) The light source device according to any one of (1) to (10), wherein the light source control unit is configured to emit laser light from the first light source in a pulse form.

(12) A subject observation system including: the light source device according to any one of (1) to (11); and an imaging device configured to capture an image of a subject illuminated with light from the light source device.

REFERENCE SIGNS LIST 1, 1A SUBJECT OBSERVATION SYSTEM
2 ENDOSCOPE
3 VOICE INPUT DEVICE
4 CONTROL DEVICE
4a VOICE INPUT TERMINAL
5 DISPLAY DEVICE
6 LIGHT SOURCE DEVICE
21 INSERTION PORTION
22 OPERATING UNIT
23 UNIVERSAL CORD
23a CONNECTOR
24 LIGHT GUIDE
25 ILLUMINATION LENS
26 IMAGING UNIT
27 ELECTRIC CABLE
31 CORD
41 INPUT UNIT
42 VIBRATION FREQUENCY DETECTING UNIT
43 MEMORY
44 IMAGE PROCESSING UNIT
45 DISPLAY CONTROL UNIT
46 LIGHT SOURCE DEVICE MAIN BODY
47 CONTROL UNIT
261 OPTICAL SYSTEM
262 IMAGING ELEMENT
263 LIGHT RECEIVING UNIT
264 READING UNIT
461 FIRST LIGHT SOURCE
462 SECOND LIGHT SOURCE
463 FIRST LIGHT GUIDE PATH
464 SECOND LIGHT GUIDE PATH
465 FIRST LIGHT SOURCE DRIVER
466 SECOND LIGHT SOURCE DRIVER
467 FIRST LIGHT AMOUNT DETECTING UNIT
468 SECOND LIGHT AMOUNT DETECTING UNIT
471 IMAGING CONTROL UNIT
472 LIGHT SOURCE CONTROL UNIT

The invention claimed is:

1. A light source device comprising:
a first light source configured to emit laser light;
a second light source configured to emit light; and
a light source control unit configured to control operations of the first light source and the second light source,
wherein the light source control unit is configured to execute each of first switching control of switching a lighting state from the first light source to the second light source and second switching control of switching the lighting state from the second light source to the first light source on laser light which is applied to a subject after emitted from the first light source based on a time reference in accordance with a class specified by a laser standard indicating a safety standard for a laser product.

2. The light source device according to claim 1, wherein the second light source is turned on after time of the time reference or more has elapsed since the first light source was turned off in the first switching control, and
the first light source is turned on after the time of the time reference or more has elapsed since the second light source was turned off in the second switching control.

3. The light source device according to claim 1, further comprising
a light amount detecting unit configured to detect a light amount of laser light emitted from the first light source and a light amount of light emitted from the second light source,
wherein, in the first switching control, a light amount of the second light source is adjusted based on a total light amount of light detected by the light amount detecting unit from a time point earlier than a present time by the time reference to the present time during a period from when the first light source was turned off to when the time reference has elapsed and an exposure emission limit set in accordance with the class, and
in the second switching control, a light amount of the first light source is adjusted based on a total light amount of light detected by the light amount detecting unit from a time point earlier than a present time by the time reference to the present time during a period from when the second light source was turned off to when the time reference has elapsed and the exposure emission limit.

4. A light source device comprising:
a first light source configured to emit laser light;
a second light source configured to emit light; and
a light source control unit configured to control operations of the first light source and the second light source,
wherein the light source control unit is configured to execute switching control of switching a lighting state from the first light source to the second light source on laser light applied to a subject after emitted from the first light source based on a time reference in accordance with a class specified by a laser standard indicating a safety standard for a laser product.

5. The light source device according to claim 4, wherein the second light source is turned on after time of the time reference or more has elapsed since the first light source was turned off in the switching control.

6. The light source device according to claim 4, further comprising
a light amount detecting unit configured to detect a light amount of laser light emitted from the first light source and a light amount of light emitted from the second light source,
wherein, in the switching control, a light amount of the second light source is adjusted based on a total light amount of light detected by the light amount detecting unit from a time point earlier than a present time by the time reference to the present time during a period from when the first light source was turned off to when the time reference has elapsed and an exposure emission limit set in accordance with the class.

7. A light source device comprising:
a first light source configured to emit laser light;
a second light source configured to emit light; and
a light source control unit configured to control operations of the first light source and the second light source,
wherein the light source control unit is configured to execute switching control of switching a lighting state from the second light source to the first light source on laser light applied to a subject after emitted from the first light source based on a time reference in accordance with a class specified by a laser standard indicating a safety standard for a laser product.

8. The light source device according to claim 7, wherein, in the switching control, the first light source is turned on after time of the time reference or more has elapsed since the second light source was turned off.

9. The light source device according to claim 7, further comprising
a light amount detecting unit configured to detect a light amount of laser light emitted from the first light source and a light amount of light emitted from the second light source,
wherein, in the switching control, a light amount of the first light source is adjusted based on a total light amount of light detected by the light amount detecting unit from a time point earlier than a present time by the time reference to the present time during a period from when the second light source was turned off to when the time reference has elapsed and an exposure emission limit set in accordance with the class.

10. The light source device according to claim 1, wherein the class is a class 2 or class 2M specified by the laser standard or a class 3R of a wavelength range of 400 to 700 nm.

11. The light source device according to claim 1, wherein the light source control unit is configured to emit laser light from the first light source in a pulse form.

12. A subject observation system comprising:
a first light source configured to emit laser light;
a second light source configured to emit light; and
a light source control unit configured to control operations of the first light source and the second light source, and
an imaging device configured to capture an image of a subject illuminated with light from the light source device,
wherein the light source control unit is configured to execute each of first switching control of switching a lighting state from the first light source to the second light source and second switching control of switching the lighting state from the second light source to the first light source on laser light which is applied to a subject after emitted from the first light source based on a time reference in accordance with a class specified by a laser standard indicating a safety standard for a laser product.

* * * * *